United States Patent [19]

Muller et al.

[11] Patent Number: 5,847,226
[45] Date of Patent: Dec. 8, 1998

[54] PROCESS FOR THE PREPARATION OF NOOTKATONE

[75] Inventors: Bernard Muller, Chambesy; Christopher Dean, Grand-Lancy, both of Switzerland; Christian Schmidt, Hamburg, Germany; Jean-Charles Kuhn, Geneva, Switzerland

[73] Assignee: Firmenich SA, Geneva, Switzerland

[21] Appl. No.: 875,885

[22] PCT Filed: Dec. 6, 1996

[86] PCT No.: PCT/IB96/01371

§ 371 Date: Aug. 7, 1997

§ 102(e) Date: Aug. 7, 1997

[87] PCT Pub. No.: WO97/22575

PCT Pub. Date: Jun. 26, 1997

[30] Foreign Application Priority Data

Dec. 18, 1995 [CH] Switzerland .............................. 3562/95

[51] Int. Cl.$^6$ .............................. C07C 45/00; C07C 35/22
[52] U.S. Cl. .......................... 568/346; 568/344; 568/349; 568/819
[58] Field of Search ............................ 549/429; 468/446; 435/28; 568/344, 346, 349, 819

[56] References Cited

U.S. PATENT DOCUMENTS 3,887,622  6/1975  Boelens et al. ...................... 260/586 P
5,030,739  7/1991  Foricher et al. .

FOREIGN PATENT DOCUMENTS 0 198 351  10/1986  European Pat. Off. ........ C07B 41/00
59-031728  5/1984   Japan .

OTHER PUBLICATIONS

Willershausen et al. Metalkalytische Transformation von Valencen zu Nootkaton, Chemiker–Zeitung, 115, 1991, pp. 356–358.
Enzymatische Transformation von Valencen zu Nootkaton, Chemiker–Zeitung, 115, pp. 358–360, 1991.

Primary Examiner—Jose G. Dees
Assistant Examiner—Alton Pryor
Attorney, Agent, or Firm—Pennie & Edmonds LLP

[57] ABSTRACT

A method for preparing nootkatone, nootkatol or mixtures thereof by oxidizing valencene, wherein the valencene is exposed to an oxygenated atmosphere in a suitable reaction medium and in the presence of an unsaturated fatty acid hydroperoxide, and the nootkatone and/or nootkatol is (are) optionally separated from the reaction medium. The method enables nootkatone yields of around 60 g per kg of reaction medium to be achieved.

17 Claims, No Drawings

PROCESS FOR THE PREPARATION OF NOOTKATONE

This application is a 371 of PCT/IB96/01371 filed Dec. 6, 1996.

TECHNICAL FIELD

The present invention relates to the field of organic synthesis and, more particularly, to a process for the preparation of nootkatone or nootkatol, or mixtures of these compounds, by oxidation of valencene, characterized in that the latter is exposed to an oxygen-containing atmosphere in an appropriate reaction medium and in the presence of a hydroperoxyde of an unsaturated fatty acid and in that, optionally, the nootkatone and/or the nootkatol is separated from the reaction mixture.

Nootkatone, or 4,4a,5,6,7,8-hexahydro-6-isopropenyl-4,4a-dimethyl-2(3H)-naphtalenone, nootkatol, or 2,3,4,4a,5,6,7,8-octahydro-6-isopropenyl-4,4a-dimethyl-2-naphtalenol, and valencene, or 1,2,3,5,6,7,8,8a-octahydro-7-isopropenyl-1,8a-dimethyl-naphthalene, the latter being used as starting material in the process of the invention, are compounds of natural origin, namely natural constituents of citrus oils, amongst which grapefruit, in which they are present in an optically active form.

Because of its excellent organoleptic qualities and in particular its typical grapefruit taste, nootkatone is a widely used ingredient in perfumery and the flavor industry. On the other hand, as a result of the legislation presently in force in most countries, relating to the use of nutrition additives, it is of capital importance to dispose of a process for the synthesis of this compound which is not only profitable and can be applied on an industrial scale, but which furthermore can supply this product in a quality which is satisfactory as regards established criteria as to its natural origin. Now, at present, such a quality can only be obtained by extraction of natural products containing nootkatone, in particular grapefruit, a method which is hardly economic.

PRIOR ART

A large number of syntheses has been described until now to obtain nootkatone by the oxidation of valencene. Amongst the oldest processes, one can cite the oxidation of valencene using tert-butyl chromate (see, for example, G. L. K. Hunter et al., in J. Food Sci. 1965, 30, 876) or tert-butyl peracetate (see C. W. Wilson et al., J. Agric. Food Chem. 1978, 26, 1430).

There are also other known chemical processes which use several reaction steps, starting from nootkatene (see, for example, Canadian patent n° 901601), cyclohexene (see M. Pesaro et al., Chem. Comm. 1968, 19, 1152) or even cyclohexadiene (see A. J. Birch, J. Agr. Food Chem. 1974, 22, 162).

Finally, the bioconversion of valencene to nootkatone catalyzed by certain microorganisms (see R. S. Dhavlikar et al., Dragoco Rep. 1973, 12, 251), or starting from vegetable cell cultures (F. Drawert et al., Plant Cell Reports 1984, 3, 37) has also been studied, but these two methods can only provide nootkatone in yields which are too low to allow a commercial exploitation.

Thus, all these known processes turn out to be either not adapted to provide a product which fulfills the established criteria with respect to its natural character, or too complicated and too expensive, thus not adapted for an industrial scale exploitation.

DESCRIPTION OF THE INVENTION

The present invention brings precisely an advantageous solution to the problem of the synthesis of nootkatone.

The above-cited process of the invention is a one-step process, of very simple execution, which can provide nootkatone in very advantageous yields and in a quality which is in conformity with the requirements for a use in food products.

We have now discovered that it is henceforth possible to obtain this product by simple oxidation of valencene in the presence of a hydroperoxyde of an unsaturated fatty acid. This transformation is executed under an oxygen-containing atmosphere and in an appropriate reaction medium, i.e. favorable for the formation of the desired product in yields which are useful for a profitable and large-scale exploitation.

Moreover, as cited above, the process of the invention also makes it possible to obtain nootkatol. The latter is also a known compound, namely cited several times as a precursor of nootkatone, both in processes for the synthesis of the latter (see, for example, GB 1 299 299), and upon its formation from cultures of vegetable cells (F. Drawert et al., reference cited). It possesses organoleptic properties which are distinct from those of nootkatone, but also showing tonalities of the citrus type.

According to the invention, as the product of the oxidation there is typically obtained a mixture of nootkatone and nootkatol, in which the relative proportions of these two compounds can vary depending on the reaction conditions. As a result of the fact that the two compounds possess similar basic organoleptic properties, the thus-obtained mixtures can be used as such for applications in the field of flavors or in perfumery. On the other hand, if desired, these compounds can be separated from the reaction product using usual techniques, like chromatography or distillation.

The oxidation reaction which characterizes the process of the invention is carried out under an oxygen atmosphere. Said atmosphere may be constituted of air, but it has been observed that the best yields in final product could be obtained when an oxygen-enriched atmosphere was used, for example a mixture of air and oxygen. According to a more preferred embodiment, an atmosphere of pure oxygen is used.

The reaction medium in the process of the invention will typically be an aqueous medium which contains the substrate and the hydroperoxyde of the unsaturated fatty acid, means being provided for allowing control of the temperature and of the pH of the medium during the reaction.

According to the invention, the hydroperoxyde of the unsaturated fatty acid can be directly added to the reaction medium, with its preparation being carried out beforehand by autoxidation or photooxidation, or by enzymatically or chemically-catalyzed oxidation of the corresponding fatty acid. Alternatively, according to a preferred embodiment of the invention, the above-mentioned hydroperoxyde can be formed in situ in the reaction medium starting from the appropriate unsaturated fatty acid. The latter will then be selected from fatty acids which are capable of forming one or several hydroperoxydes under the reaction conditions. For this purpose, on can cite, for example, linoleic acid or linolenic acid, or natural origin precursors of said acids, such as the hydrolysates from linseed or sunflower oil. Hydrolysates from fish oil, or the polyunsaturated fatty acids contained therein, may also be used. Excellent yields in the desired final product were obtained, for example, with linoleic acid or its hydroperoxydes, namely 13-hydroperoxylinoleic acid.

The formation of the hydroperoxyde may also take place with a monounsaturated fatty acid, for example oleic acid.

When the hydroperoxyde is formed in situ starting from a polyunsaturated fatty acid, according to a preferred embodiment of the invention, there is added a lipoxygenase to the reaction medium. We have observed that the addition of a lipoxygenase increased the efficiency of the process by promoting a more rapid oxidation of the above-mentioned fatty acid, and thus as an accelerated formation of the hydroperoxyde which oxidizes the valencene. The lypoxygenase may be added, for example, in the form of soya flour which is typically obtained by grinding soya beans. When the soya flour has not been defatted beforehand, it shows the further advantage of bringing in polyunsaturated fatty acids which are capable of forming hydroperoxydes under the reaction conditions.

It has however been found that the use of lipoxygenase in a purified form made it possible to obtain yields of final product which were even more advantageous and it avoided possible problems related to a viscosity of the reaction medium which is too high. Thus, a lipoxygenase from soya flour can be used, amongst those which are available commercially in purified form and, typically, freeze-dried. The examples described below cite lipoxygenases which are perfectly convenient for the purposes of the invention. Lipoxygenases from other sources than soya flour may be used as well.

Moreover, it has been observed that the oxidation of valencene could also be accelerated by addition, to the reaction medium containing the unsaturated fatty acid, of a catalyst capable of promoting the formation of radicals, for example copper powder, copper stearate or yet cobalt naphthenate.

The temperature at which the oxidation of valencene takes place may vary within a wide range of values. For this purpose, one can cite temperatures varying between 20° and 80° C. It was surprisingly observed that temperatures of the order of 50° or more gave particularly advantageous results.

The reaction can be carried out at a pH value comprised between about 5.0 and 10. We observed that the pH of the medium could have an influence on the composition of the reaction product and favor the formation of one or the other of the desired products, namely nootkatone and nootkatol. On the other hand, when a lipoxygenase is added, the pH may also be chosen as a function of the source of said lipoxygenase.

As will be apparent from the examples presented further on, when using lipoxygenases from soya flour, the best yields of nootkatone were obtained at pH-values comprised between 7.5 and 9.5, whereas lower pH-values allowed the production of a higher proportion of nootkatol. It is therefore possible to obtain essentially nootkatone by running the reaction at pH-values of the order of 7.5 to 9.5 and, preferably, at a pH of about 8, whereas a lower pH makes it possible to obtain a higher amount of nootkatol in the reaction mixture. This has the advantage that the separation step according to the process of the invention can be avoided, one or the other of the said compounds being obtained in an almost pure state, or, in any case, in a highly preponderant amount, in particular in the case of nootkatone. As was cited beforehand, the mixtures of nootkatone and nootkatol which are directly obtained from the reaction are useful flavoring ingredients as such, their organoleptic properties not being strongly dependent on the relative proportions of these two compounds. It is however clear that their properties will vary somewhat as a function of these relative proportions. Thanks to the process of the invention, there can thus be obtained a wide range of products, including the two above-mentioned compounds in an essentially pure state, as well as their mixtures containing various relative proportions of these two components.

It should also be noticed that reaction products containing a certain amount of starting material, i.e. valencene, can be obtained, and this depending, of course, on the reaction time. The valencene can be separated from the reaction mixture as will be described in detail in the examples. It is, however, not deleterious to the organoleptic properties of the mixture, such that said separation may also be superfluous.

Another by-product which can be formed under the reaction conditions, however in smaller amounts, typically below 10 weight % with respect to the weight of the reaction product, is the epoxyde of valencene or 1,8a-epoxy-6-isopropenyl-4,4a-dimethyl-naphthalene.

Although it has been found that the best yields of, for example, nootkatone were obtained when the pH was held constant and comprised between 8 and 9 during the whole reaction time, satisfying results were also obtained when the pH of the medium was adjusted to a value of the order indicated above at the beginning of the reaction, without being subsequently readjusted during the reaction.

According to a more preferred embodiment of the invention, the oxidation of valencene is carried out under a pure oxygen atmosphere and at a temperature comprised between 50° et 80 ° C., while the pH of the reaction medium was held at a value comprised between 8 and 9.5 during the total reaction time.

The invention thus provides a process allowing the production of useful flavoring ingredients of various qualities, ingredients which are composed of nootkatone or of nootkatol in an essentially pure state, of their mixtures, or even of mixtures of these compounds with valencene. By using this process, nootkatone could be obtained in concentrations of the order of at least 20 to 30 g/kg of reaction mixture, which, in the best cases, could go up to 60 g/kg, or even more.

The invention will now be described in more detail by means of the following examples, in which the temperatures are indicated in degrees centigrade and the abbreviations have the meaning usual in the art.

EMBODIMENTS OF THE INVENTION

EXAMPLE 1

The oxidation of valencene was carried out according to the general method described hereafter.

General method

A mixture of sodium phosphate buffer having pH 8.5, valencene and an unsaturated fatty acid in the desired proportion is gently stirred in a 6-necked flask which is equipped with a stirrer, a thermometer, a pH-control device (PHstat), a dropping funnel and an inlet for air and/or oxygen. When pure oxygen was used, as is the case in most of the runs which are cited in the Table below, the mixture was first degassed and purged three or four times under vacuum, then replaced with an oxygen atmosphere, and the stirrer speed was increased to 750 rpm. Optionally, the lipoxygenase which is contained in the dropping funnel, and which may be dissolved in a buffer solution, is added in one go. A slight oxygen overpressure is maintained during the course of the reaction, such as to allow the taking of samples for analysis and follow-up of the reaction without air contamination. If desired, during the reaction, the pH is kept at a constant value by automatic addition of an aqueous NaOH-solution. After the desired reaction time, if necessary, the mixture is cooled to room temperature, then extracted with ether (3×200 ml), washed with an aqueous 10% NaOH solution and then to neutrality with brine. The combined organic phases are dried over $Na_2SO_4$ and concentrated under vacuum. The crude mixture thus obtained is then analyzed by chromatography. It typically contains nootkatol, nootkatone and unreacted valencene, and possibly minor amounts of the epoxyde of the latter.

The valencene can be easily separated from the reaction product by treatment with silica gel, as follows: the product is dissolved in hexane and Kieselgel 60 is added to the solution, while stirring for about 5 minutes. The thus-obtained suspension is filtered through a fritted-glass filter. The silica gel is then washed with hexane (2×). The combined extracts, after concentration under vacuum, give the desired valencene.

Nootkatone and nootkatol are separated from the remaining mixture by chromatography over silica gel, the latter mixture being obtained by desorption from the silica gel using ether.

The starting materials used according to the above-described method had the following characteristics:

(+)-Valencene: GC-purity 79.5–85% ; $[\alpha]_D^{20}$=+96.5°–+108.8°; prepared by fractional distillation of valencene which had been obtained by extraction of citrus oils (origin: Firmenich Citrus Center, Florida, USA)

Lipoxygenase: Lipoxydase Type I-S; origin Sigma Chem. #L 8383 Lipoxydase Type I-B; origin Sigma Chem. #L 7395

Soya flour: obtained from freshly-ground soya beans by using an Urschel Comitrol type grinder equipped with a head of the "di-O-cut" type.

Defatted soya flour: Type I; not roasted; origin Sigma Chem. #S 9633

Fatty acids: Nouracid HE-30 ; origin AKZO Nobel, containing 64.5% of linoleic acid (sunflower oil hydrolysate) Pure (origin: Fluka) or technical (Nouracid LE-80; origin: AKZO Nobel; containing 48.2% of linolenic acid +16.3% of linoleic acid) linoleic acid. Oleic acid (origin: Fluka; 65%)

Analytical methods

The collected aliquots were treated as follows: to 500 mg of the reaction mixture to be analyzed there were added 0.4 g of NaCl, followed by an extraction with 1 ml of ether. After centrifuging, the organic layer is injected into a gas chromatography apparatus under the following conditions:

Spwax 10 column; 0,53 i.d., 15 m length, 100° over 1 min and then up to 200° at 5°/min. Column Spb-1; 0,53 i.d., length 15 m, 100° over 1 min, and then to 160° at 5°/min.

In a typical run, it was proceeded as described above, by using 50 g of a sodium phosphate buffer of pH 8.5 (0.1M), 10 g of valencene, 4.0 g of fatty acid and 600 mg of lipoxygenase of Type I-S in 5 g of sodium phosphate buffer of pH 8.5. The reaction was carried out under a pure oxygen atmosphere, while maintaining the temperature at 60°. After 48 h of reaction time and the treatment described above, 9.41 g of a product were obtained, the chromatographic analysis of which showed that it contained 20.2% of nootkatone, 10.1% of nootkatol and 43.9% of unreacted valencene (the remainder being valencene epoxyde). This corresponds to a nootkatone yield of about 27.3 g per kg of reaction mixture. The above-mentioned reaction product was taken up in 150 ml of hexane and treated with 75 g of Kieselgel 60 (origin: Merck). After filtration and washing with hexane (2× with 75 ml), the extracts were concentrated to obtain 3.61 g of valencene having a purity of 86%. The desorption of the silica gel gave 4.75 g of a mixture containing 43% of nootkatone, which corresponds to a yield of 29.9% based on valencene.

An identical run in which a higher amount of fatty acid, namely 6 g, was used, gave, after a 24 h reaction time and the usual treatment, 9.55 g of a product containing 16.1% of nootkatone, 13.5% of nootkatol and 41.6% of unreacted valencene. This corresponds to a yield of 21.5 g of nootkatone and 18.0 g of nootkatol per kg of reaction mixture. These products were obtained in a pure state by chromatography over $SiO_2$, using a 9:1 hexane/ether mixture as eluent.

EXAMPLE 2

A mixture of 46.4 g of water, 3.6 g of a 10% aqueous NaOH-solution, 10.0 g of valencene and 4.0 g of a polyunsaturated fatty acid was gently stirred in a 6-neck flask equipped with a magnetical stirrer, a thermometer, a pH-control device, a dropping fimnel and an oxygen inlet. The mixture was degassed and purged under vacuum (3×), and a pure oxygenated atmosphere was applied. A solution of 600 g of lipoxygenase Type I-S in 5 g of a sodium phosphate buffer of pH 8.5, which was contained in the dropping fhnnel, was added in one go and stirring increased to 750 rpm. The pH was automatically maintained (PHstat) at a value of 8.0 during the whole reaction by adding a 5% aqueous NaOH solution. A slight $O_2$-overpressure was maintained during the entire reaction to allow taking of samples without air contamination. The temperature was maintained at 60°.

After 24 h, the reaction mixture was cooled to room temperature, then extracted with ether (3×200 ml), washed with a 10% aqueous NaOH solution and then to neutrality with brine. The combined organic phases were dried over $Na_2SO_4$ and concentrated under vacuum. The thus obtained product (8.86 g) contained 41.7% of nootkatone, 9.9% of nootkatol and 13.4% of unreacted valencene. This corresponds to the formation of 53.1 g of nootkatone per kg of reaction mixture.

EXAMPLES 3–29

Valencene was oxidized according to the method described in Example 1 or 2, varying the reaction parameters as indicated in the Table hereafter. The concentrations or yields are given in g per kg of reaction mixture or in % of the product obtained. All reactions were carried out under a pure oxygen atmosphere, unless indicated otherwise. The fatty acid used was a hydrolysate of sunflower oil as cited in Example 1, unless indicated otherwise. The indicated pH-value corresponds to the initial pH of the medium, non-adjusted during the reaction time, unless indicated otherwise.

TABLE I

| Run | Valencene conc. g/kg | Lipoxygenase (source or purified) | Fatty acid g/kg | pH | Temp. °C. | Reaction time h | Unreacted valencene % | Yield of nootkaton g/kg | Yield of nootkaton % | Yield of nootkatol g/kg | Yield of nootkatol % |
|---|---|---|---|---|---|---|---|---|---|---|---|
| 3 | 10.9 | soya flour | — | 8.5 | ~25 | 24 | 89 | 0.16 | 1.47 | 0.17 | 1.52 |
| 4 | 10.9 | defatted soya flour | — | 8.5 | ~25 | 24 | 98.2 | 0.02 | 0.2 | 0.02 | 0.22 |
| 5 | 10.9 | soya flour | 4.3 | 8.5 | ~25 | 24 | 81,5 | 0.33 | 3.03 | 0.12 | 1.09 |
| 6 | 46.6 | Type I-S[a)] | — | 8.5 | ~25 | 24 | 100 | — | — | — | — |
| 7 | 46.6 | Type I-S[a)] | 18.6 | 8.5 | ~25 | 24 | 77 | 1.12 | 2.4 | 0.67 | 1.43 |
| 8 | 46.6 | Type I-B[a)] | 18.6 | 8.5 | ~25 | 24 | 82 | 1.17 | 2.5 | 0.61 | 1.3 |
| 9* | 46.6 | Type I-S[a)] | 18.6 | 8.5 | ~25 | 24 | 92.9 | 0.15 | 0.32 | 0.09 | 0.19 |
| 10 | 46.6 | Type I-S[a)] | 18.6 | 6.5[c)] | ~25 | 48 | 81.3 | 1.11 | 2.37 | 0.68 | 1.45 |
| 11 | 46.6 | Type I-S[a)] | 18.6 | 7.0[c)] | ~25 | 48 | 79.6 | 1.1 | 2.35 | 0.76 | 1.64 |
| 12 | 46.6 | Type I-S[a)] | 18.6 | 7.5[c)] | ~25 | 48 | 78.3 | 1.34 | 2.86 | 0.79 | 1.7 |
| 13 | 46.6 | Type I-S[a)] | 18.6 | 8.0[c)] | ~25 | 48 | 82.8 | 1.67 | 3.58 | 0.87 | 1.86 |
| 14 | 46.6 | Type I-S[a)] | 18.6 | 8.5[c)] | ~25 | 48 | 79.6 | 1.62 | 3.47 | 0.94 | 2.01 |
| 15 | 46.6 | Type I-S[a)] | 18.6 | 9.0[c)] | ~25 | 48 | 77.9 | 1.62 | 3.47 | 0.85 | 1.83 |
| 16 | 143.7 | Type I-S[b)] | 57.5 | 8.5 | 15 | 24 | 89.5 | 1.08 | 0.75 | 0.93 | 0.65 |
| 17 | 143.7 | Type I-S[b)] | 57.5 | 8.5 | 25 | 24 | 85.7 | 2.26 | 1.57 | 1.52 | 1.06 |
| 18 | 143.7 | Type I-S[b)] | 57.5 | 8.5 | 35 | 24 | 82 | 3.68 | 2.56 | 3.12 | 2.17 |
| 19 | 143.7 | Type I-S[b)] | 57.5 | 8.5 | 40 | 24 | 73.5 | 4.53 | 3.15 | 3.97 | 2.76 |
| 20 | 143.7 | Type I-S[b)] | 57.5 | 8.5 | 45 | 24 | 75 | 6.51 | 4.53 | 5.43 | 3.78 |
| 21 | 143.7 | Type I-S[b)] | 57.5 | 8.5 | 50 | 24 | 58.5 | 9.47 | 6.59 | 7.16 | 4.98 |
| 22 | 143.7 | Type I-S[b)] | 57.5 | 8.5 | 60 | 24 | 46.3 | 26.94 | 18.75 | 14.63 | 10.18 |
| 23 | 143.7 | — | — | 8.5 | 60 | 24 | 89.9 | 0.12 | 0.08 | 0.08 | 0.05 |
| 24 | 143.7 | — | 57.9 | 8.5 | 60 | 24 | 47 | 19.25 | 13.28 | 11.3 | 7.8 |
| 25** | 143.7 | Type I-S[b)] | — | 8.5 | 60 | 24 | 53 | 18.76 | 13.41 | 11.44 | 8.18 |
| 26 | 143.7 | Type I-S[b)] | 57.5 | 8.5 | 70 | 24 | 30 | 30.53 | 21.25 | 14.22 | 9.9 |
| 27 | 143.7 | Type I-S[b)] | 57.5*** | 8.5 | 70 | 24 | 60.6 | 10.47 | 7.29 | 7.87 | 5.48 |
| 28 | 143.7 | Type I-S[b)] | 57.5 | 8.0[c)] | 70 | 24 | 14 | 57.48 | 40.01 | 13.62 | 9.48 |
| 29 | 143.7 | Type I-S[b)] | 57.5 | 8 | 70 | 24 | 28.4 | 34.71 | 24.16 | 13.66 | 9.51 |

*air atmosphere
**addition of 91.2 g of 13-hydroperoxylinoleic acid per kg of reaction mixture
***linolenic acid
[a)] 2.79 g/kg of reaction mixture
[b)] 8.62 g/kg of reaction mixture
[c)] pH maintained constant during the reaction

EXAMPLE 30

A. The hydroperoxyde of the fatty acid was prepared separately as follows. In a five-neck flask equipped with a mechanical stirrer, an $O_2$-inlet, a probe for pH-control, a dropping funnel and a powder funnel, there were charged 262.0 g of water, 10.3 g of NaOH in a 10% solution in water and 33.7 g of Nouracid HE-30, and the whole was mixed at 20°. The pH was adjusted to 9.5, a value which was maintained throughout the entire reaction by addition of a 10% aqueous NaOH-solution. After purging 3× with oxygen, 33 g of freshly ground soya flour where then added. The mixture was allowed to react for 1 h, after which time a iodometric titration analysis (titration system: $Na_2S_2O_3$ 0.01M, KI, $CH_3COOH/CHCl_3$ 2:3) of a sample of 500 mg of the reaction mixture indicated a yield of 88% of hydroperoxyde, i.e. of 13-hydroperoxylinoleic acid, corresponding to a content in hydroperoxyde of 63.0 g per kg of reaction mixture. The thus-obtained hydroperoxyde suspension was decanted (alternatively, the solid may be separated by filtration and the filtrates recovered) for 1 h and the decanted liquid separated. The remaining flour was washed with water (306 g), stirred for 1 min and again decanted for 1 h. The decanted liquid was again separated and added to the first liquid which had been obtained beforehand. The thus-obtained solution containing 32 g of hydroperoxyde per liter of solution (filtration), was used in the oxidation of valencene, as described below.

B. In a five-neck flask equipped with a mechanical stirrer, an oxygen inlet, a thermometer and a device for pH-control (pH-electrode and automatic NaOH-addition device), heated by means of an oil bath, there were charged 44 g of the hydroperoxyde solution prepared under A, 6.0 g of valencene and 1 drop of an antifoaming agent (Dow Corning® FG-10). The mixture was purged 4× with oxygen, the pH was adjusted to 8 and the temperature to 70°. The mixture was reacted while maintaining the pH at a value of 8, as indicated in Example 1. The progress of the reaction was monitored by gas chromatographic analysis of aliquots taken and analyzed as indicated in Example 1. These analyses (column of type Spb-1, 15 m, 100° 1 min, then 100°–160° at 5°/min, retention time of nootkatone 12.63 min) showed a content of 34.56 weight % of nootkatone and of 9.47% of nootkatol in the reaction product after 24 h, while these values were respectively of 44.43% and 7.94% after 48 h of reaction time.

The reaction was stopped after 48 h, the pH was adjusted to 12, the mixture was extracted with 125 ml of cyclohexane, then with 125 ml of cyclohexane plus 10% NaCl. The organic phases were washed to neutrality by using 2×50 ml of $H_2O$+1% NaCl. The solution (about 300 ml) was filtered over 22 g of $SiO_2$ (Chromagel® 60 silica, 70–200 μm) and the product distilled in a bulb-to-bulb apparatus (150°/10 Pa) to give about 3.2 g of concentrated product ($[\alpha]_D^{20}$=+ 129.40° (2% in $CHCl_3$) ).

The yield of nootkatone after 48 h of reaction and separation from the reaction medium was 53.3 g per liter of reaction mixture.

EXAMPLES 31–44

The reactions were conducted as described in Example 2 or 30, i.e. by preparing the hydroperoxyde in-situ, respectively separately, but varying either the starting fatty acid or the reaction conditions, as indicated in the Table below. All reactions were carried out under a pure oxygen atmosphere, at a constant pH of 8 and a temperature of 70°, during 48 h. The results obtained are given in the Tables below. The concentrations indicated are understood to be relative to the reaction mixture and before separation of the latter. When the hydroperoxydes were prepared by photooxidation of the corresponding fatty acids, the reaction conditions were similar to those previously described, with the only difference that the mixture of the fatty acid and the sensitizer (Rose bengale) was irradiated under an oxygen atmosphere using a lamp of the Philips HPK 125 W BA 15 D Type 57203 B9 type.

TABLE II

| Run | Execution mode | Valencene conc. g/kg | Catalyst mg/kg | Fatty acid or hydroperoxyde g/kg | Yield of nootkatone g/kg |
|---|---|---|---|---|---|
| 31 | Ex. 2 | 156.1 | Cu-stearate (781) | Linoleic acid (40.3) | 37.8 |
| 32 | Ex. 2 | 156.1 | Co-naphthenate (781) | Linoieic acid (40.3) | 55.2 |
| 33 | Ex. 2 | 156.1 | Cu-powder (781) | Linoleic acid (40.3) | 28.8 |
| 34 | Ex. 2 | 154.9 | Cu-stearate (775) | Oleic acid (10.1) | 56.2 |
| 35 | Ex. 2 | 154.9 | Cu-naphthenate (775) | Oleic acid (10.1) | 57.8 |
| 36 | Ex. 2 | 155.8 | Cu-powder (3115) | Oleic acid (40.5) | 41 |
| 37* | Ex. 30 | 161.3 | Rose bengale | Linoleic acid (40.1) | 39.5 |
| 38* | Ex. 30 | 161.3 | Rose bengale | Oleic acid (40.4) | 47.1 |
| 39 | Ex. 30 | 153.8 | — | 13-HPOD (16.2) | 56.6 |
| 40 | Ex. 2 | 172.2 | Soya flour (86'580) | Linoleic acid (11.2) | 38 |
| 41 | Ex. 30 | 153.8 | — | 13-HPOD**[1]) (27.7) | 41.2 |
| 42 | Ex. 30 | 120 | — | 13-HPOD**[2]) (27.3) | 55 |
| 43 | Ex. 30 | 120 | — | 13-HPOT** (27.0) | 47.6 |
| 44 | Ex. 30 | 120 | — | 13-HPOD**[3]) (20.2) | 14.5 |

*run using hydroperoxydes prepared by photooxidation
**13-HPOD = 13-hydroperoxylinoleic acid
13-HPOT = 13-hydroperoxylinolenic acid
[1])decanted 13-HPOD sol.
[2])filtered 13-HPOD sol.
[3])centrifuged 13-HPOD sol.

We claim:

1. Process for the preparation of nootkatone or nootkatol, or of mixtures of these compounds, by oxidation of valencene, characterized in that the latter is exposed to an oxygen-containing atmosphere in an appropriate reaction medium and in the presence of a hydroperoxide of an unsaturated fatty acid and in that, optionally, the nootkatone and/or the nootkatol is separated from the reaction mixture.

2. Process according to claim 1, characterized in that the fatty acid is a polyunsaturated fatty acid.

3. Process according to claim 1, characterized in that the oxidation of valencene is carried out under a pure oxygen atmosphere.

4. Process according to claim 2, characterized in that the oxidation of valencene is carried out in the presence of a hydroperoxyde of linoleic or of linolenic acid.

5. Process according to claim 1, characterized in that the oxidation of valencene is carried out in the presence of a hydroperoxyde of oleic acid.

6. Process according to claim 1, characterized in that the temperature of the reaction medium is maintained at a value of between 20° and 80° C.

7. Process according to claim 6, characterized in that the temperature is of the order of 50° C. or higher.

8. Process according to claim 1, characterized in that the pH of the reaction medium has a value of between 5 and 10.

9. Process according to claim 8, characterized in that the pH has a value of about 8 and in that essentially nootkatone is obtained.

10. Process according to claim 1, characterized in that the oxidation of valencene is carried out under a pure oxygen atmosphere and at a temperature of between 50° and 80° C., the pH of the reaction medium being maintained at a value of between 8 and 9.5.

11. Process for the preparation of nootkatone or nootkatol, or of mixtures of these compounds, by oxidation of valencene, characterized in that valencene is exposed to an oxygen-containing atmosphere in an appropriate reaction medium and in the presence of a hydroperoxide of an unsaturated fatty acid, wherein the nootkatone and/or the nootkatol is optionally separated from the reaction mixture, and said hydroperoxide is formed in situ in the reaction medium from the unsaturated fatty acid.

12. Process according to claim 11, characterized in that the unsaturated fatty acid is oleic acid, linoleic acid, linolenic acid or one of their natural origin precursors.

13. Process according to claim 11, characterized in that there is added to the reaction medium a catalyst susceptible of promoting the formation of said hydroperoxyde.

14. Process according to claim 13, characterized in that the fatty acid is a polyunsaturated fatty acid and the catalyst is a lipoxygenase.

15. Process according to claim 13, characterized in that the catalyst is copper powder, copper naphthenate or copper stearate.

16. Process according to claim 13, characterized in that the hydroperoxyde is formed by photooxidation of the unsaturated fatty acid in the presence of Rose bengale.

17. Process for the preparation of nootkatone or nootkatol, or of mixtures of these compounds, by oxidation of valencene, characterized in that the valencene is exposed to an oxygen-containing atmosphere in an appropriate reaction medium and in the presence of a hydroperoxide of an unsaturated fatty acid, with the nootkatone and/or the nootkatol is optionally separated from the reaction mixture, the valencene is used in the form of one of its optically active isomers, and the corresponding optically active isomer of nootkatone and/or nootkatol is obtained.

* * * * *

UNITED STATES PATENT AND TRADEMARK OFFICE
CERTIFICATE OF CORRECTION

PATENT NO. : 5,847,226

DATED : December 8, 1998

INVENTORS : Bernard Muller et al.

It is certified that error appears in the above-identified patent and that said Letters Patent is hereby corrected as shown below:

On the title page: at [86] change the § 371 and § 102(e) dates from "Aug. 7, 1997" to --Aug. 6, 1997--.

Column 12, line 4: change "with" to --wherein--.

Signed and Sealed this

Twenty-fifth Day of May, 1999

Attest:

Attesting Officer

Q. TODD DICKINSON

Acting Commissioner of Patents and Trademarks